United States Patent [19]

De La Cruz et al.

[11] Patent Number: 5,693,874
[45] Date of Patent: Dec. 2, 1997

[54] TEST APPARATUS AND METHOD FOR DETERMINING DEPOSIT FORMATION CHARACTERISTICS OF FUELS

[75] Inventors: Jose L. De La Cruz, San Antonio, Tex.; Ronald M. Estefan, deceased, late of San Antonio, Tex., by Carlie A. Estefan, executrix

[73] Assignee: Southwest Research Institute, San Antonio, Tex.

[21] Appl. No.: 730,672

[22] Filed: Oct. 11, 1996

[51] Int. Cl.[6] .................. G01N 11/00; G01N 5/00
[52] U.S. Cl. .............. 73/61.62; 73/61.65; 73/60.11; 73/61.72
[58] Field of Search ................ 73/61.62, 61.64, 73/61.65, 60.11, 61.72

[56] References Cited

U.S. PATENT DOCUMENTS

| | | | |
|---|---|---|---|
| 3,982,503 | 9/1976 | Keranen | 123/32 EA |
| 4,426,880 | 1/1984 | Watters et al. | 73/61.2 |
| 4,466,277 | 8/1984 | Baier et al. | 73/61.2 |
| 4,535,622 | 8/1985 | Yeoman et al. | 73/61.2 |
| 4,686,854 | 8/1987 | Herman | 73/86 |
| 4,721,081 | 1/1988 | Krauja et al. | 123/298 |
| 5,036,699 | 8/1991 | Fikentscher et al. | 73/61.2 |
| 5,068,196 | 11/1991 | Hays et al. | 436/6 |
| 5,287,731 | 2/1994 | Florkowski et al. | 73/53.05 |
| 5,299,449 | 4/1994 | Hardy et al. | 73/61.62 |
| 5,492,005 | 2/1996 | Homan et al. | 73/61.62 |

*Primary Examiner*—Hezron E. Williams
*Assistant Examiner*—J. David Wiggins
*Attorney, Agent, or Firm*—Jenkens & Gilchrist

[57] ABSTRACT

A test apparatus includes a test chamber adapted to support a test piece having the shape characteristic of an engine intake valve. Means are provided for heating the test piece, delivering a selected test fuel to the test chamber at a controlled rate and at selected intervals, and for delivering a flow of heated air through the test chamber at a preselected temperature and volumetric rate. A method for determining the relative ability of a fuel to form deposits on an engine intake valve includes placing a test piece having the shape characteristics of an engine intake valve in a test chamber, heating and maintaining the test piece at a predetermined temperature, passing a stream of heated air through the test chamber at a controlled temperature and flow rate, and alternately repeatably spraying a sample fuel onto the test piece and drying the test piece, for a period of time sufficient to establish the deposit-forming characteristics of the sample fuel.

14 Claims, 3 Drawing Sheets

TEST APPARATUS AND METHOD FOR DETERMINING DEPOSIT FORMATION CHARACTERISTICS OF FUELS

BACKGROUND OF THE INVENTION

1. Field of the Invention

This invention relates generally to a test apparatus and method for determining the relative deposit-forming characteristics of various fuels on engine valves, and more particularly to such an apparatus and method wherein the engine valve and a test chamber are separately maintained at a selected temperature.

2. Description of the Prior Art

Fuel-related valve deposits, and in particular intake valve deposits (IVD) are a source of concern for the automotive and oil industries. It has been found that fuels containing certain reactive compounds react on hot intake valve surfaces, and the resulting deposits cause increased exhaust emissions, reduced fuel economy, and driveability problems.

Currently, all of the major fuel marketers and additive manufacturers are making efforts to have their products certified by passing the "BMW" test. In this test, a vehicle is driven on the test fuel for 10,000 miles, after which the vehicle's engine is disassembled and the condition of the intake valves examined. This test is relatively expensive, typically costing on the order of at least $15,000 to test a single fuel. The currently recognized "BMW" test is also time-consuming in that a vehicle has to be driven in a prescribed manner for 10,000 miles. Furthermore, the test results are often difficult to reproduce with the same results due to atmospheric, environmental, mechanical and driver dissimilarities.

The present invention is directed to overcoming the above problems. It is desirable to have a simple, relatively quick and inexpensive test apparatus and method whereby the relative deposit-forming characteristics of various fuels can be easily and repeatably determined. It is also desirable to have such a test apparatus and method wherein the test parameters are controllable to produce optimum deposit formation and thereby reduce the amount of time required to produce measurable data.

SUMMARY OF THE INVENTION

In accordance with one aspect of the present invention, a test apparatus includes a test piece having a shape that is characteristic of an engine intake valve and is supported by a fixture disposed within a chamber. The test apparatus has a means for heating the test piece and a means for sensing the temperature of the test piece and controlling the heating means. A fuel injector is disposed in fluid communication with the chamber and is arranged to spray fuel onto a predetermined surface area of the test piece. The test apparatus further includes a means for pressurizing a preselected fuel and delivering the preselected fuel to the fuel injector, and a means for heating a flowing stream of air to a selected temperature and directing the stream of heated air through the chamber.

Other features of the test apparatus include rotating the test piece while supported within the chamber, and mixing at least one of nitrogen, nitric oxide, sulfur dioxide and sludge vapors with the flowing stream of air.

In accordance with another aspect of the present invention, a method for determining the relative ability of a fuel to form deposits on an engine intake valve include placing a test piece having the shape characteristic of an engine valve into a chamber, heating the test piece and maintaining the test piece at a predetermined temperature, and flowing a stream of heated air through the chamber at a preselected rate. The method further includes alternately injecting a controlled amount of a selected fuel onto the test piece at a predetermined rate and interrupting the injecting of fuel for a predetermined period of time. The steps of injecting fuel and interrupting the injecting of fuel is repeated, while continuously maintaining the test piece at the predetermined temperature and flowing a stream of heated air through the chamber, for a time sufficient to establish the deposit-forming characteristic of the selected fuel.

Other features of the method for determining the relative ability of a fuel to form deposits on an engine intake valve include rotating the test piece while carrying out the method, and mixing at least one of nitrogen, nitre oxide, sulfur dioxide and sludge vapors to the stream of heated air flowing through the chamber.

DESCRIPTION OF THE PREFERRED EMBODIMENT

Figure 1:
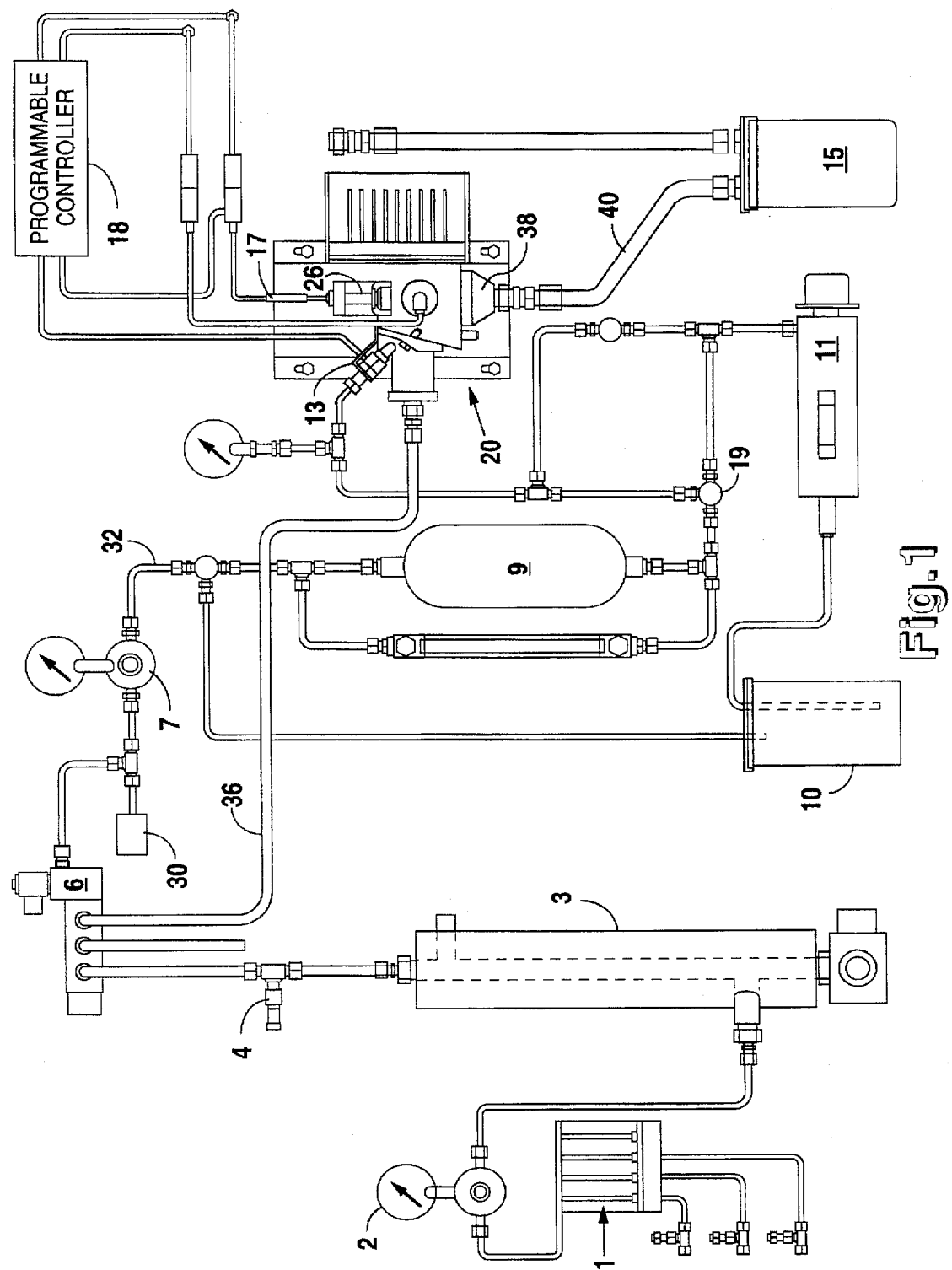
FIG. 1 is a schematic drawing showing the components of the test apparatus comprising the present invention.
Figure 2:
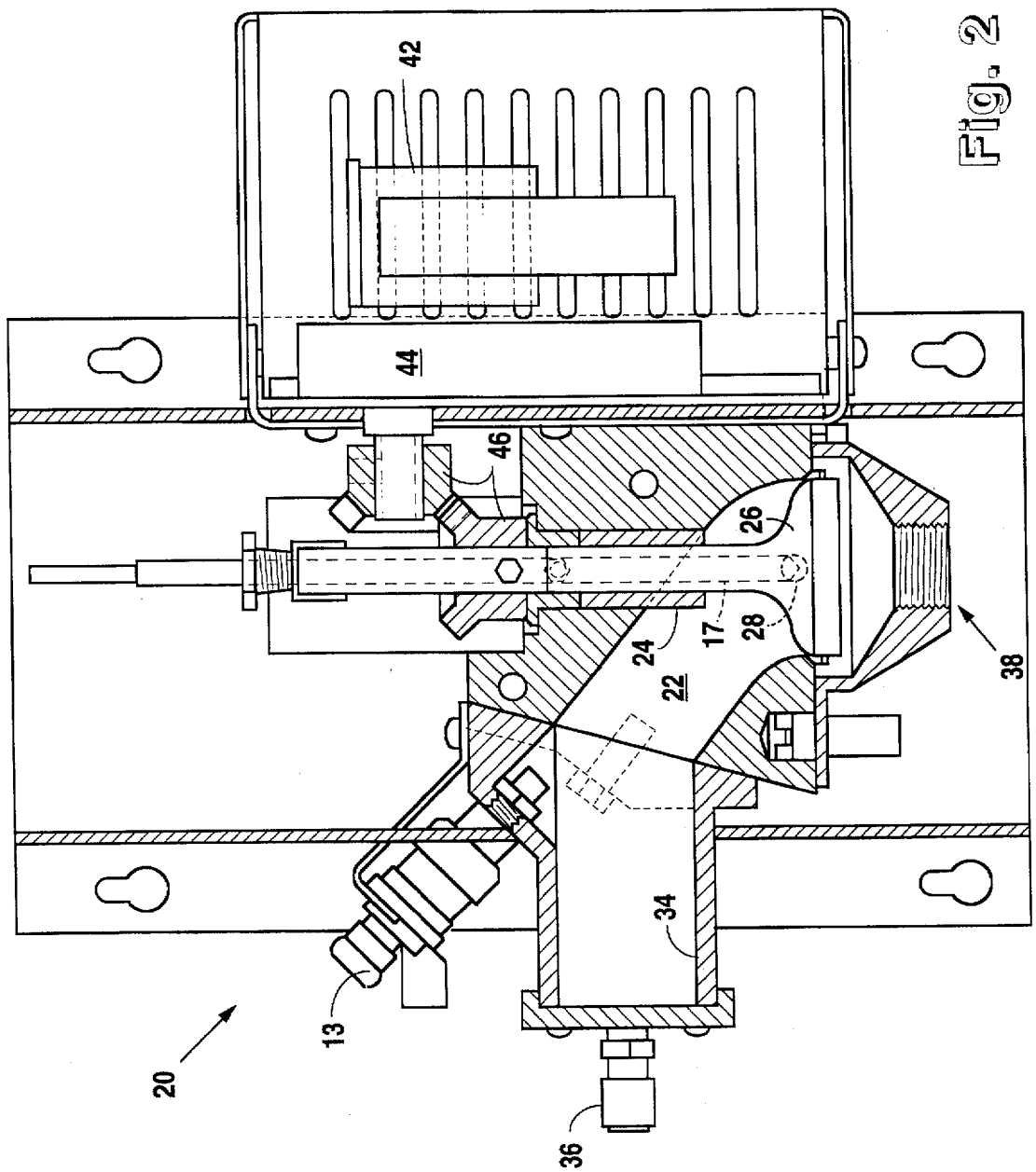
FIG. 2 is a sectional view of the test chamber of the test apparatus embodying the present invention.

The primary components of the test apparatus embodying the present invention are shown schematically in FIG. 1. A test chamber 20, as best shown in FIG. 2, has an internal air passageway 22 that is representative of a typical intake manifold of an automotive engine. A bushing 24 is disposed within the chamber 20 and serves as a fixture to removably support a test piece 26 within the chamber 20. The test piece 26 is shaped to simulate the actual external configuration of a typical intake valve of an automotive engine. The test piece 26 has an internal bore in which an electrical resistance heating element 17 in the form of a cartridge heater, with a thermocouple 28 positioned at its distal end, is centrally disposed. The heating element 17 provides a means for heating the test piece 26. The thermocouple 28, and a programmable controller 18 to which the heating element 17 and thermocouple 28 are operatively connected as shown in FIG. 1, comprise a means by which the test piece 26 can be heated to, and maintained at, a desired preselected temperature. In the preferred embodiment of the present invention, the programmable controller 18 is a Class 8005 Model 50 Programmable Controller System produced by Square D Company.

A fuel injector 13 is mounted in one side of the test chamber 20 in fluid communication with the internal passageway 22, and is arranged so that the fuel injector 13 is able to spray fuel onto the flanged head portion of the test piece 26. A predetermined amount of a selected fuel, i.e., the fuel to be tested for deposition tendencies and characteristics, is pumped from an external supply source 10 by a fuel pump 11 into a reservoir 9. In the preferred embodiment of the present invention, the reservoir 9 is a stainless steel enclosed reservoir having a capacity of 2.25 liters. The sample fuel within the reservoir 9 is pressurized by nitrogen which is provided by a source 30, regulated to a desired pressure by a pressure regulator 7 which, in the preferred embodiment, is set to control downstream line pressure to 38 psig, and then delivered to the reservoir 9 by a conduit 32 extending between the pressure regulator 7 and the reservoir 9. This arrangement assures delivery of the test fuel to the fuel injector 13 at a uniform constant pressure without the transient pressure pulses often observed in systems which rely on mechanical pumps to provide fuel pressure. In carrying out the test, a predetermined amount of the test fuel is metered through the fuel injector 13 by the programmable controller 18 which also controls the amount of time the injector 13 is open.

Heated air is supplied to an inlet port 34 in the chamber 20 by a system that includes, as best shown in FIG. 1, a flow meter 1 that receives air from one or more pressurized sources, a pressure regulator 2, and a heat exchanger 3 whereat the pressurized air is heated to a desired temperature. The heated air is then directed past a relief valve 4, and controllably directed to a conduit 36 in fluid communication with the inlet port 34 in the test chamber 20 by a directional valve 6. After entering the test chamber 20, by way of the inlet port 34, the air stream flows through the internal air passageway 22, around the test piece 26, then past the head of the test piece 26 around a small clearance provided between the perimeter of the head of the test piece 26 and the air passageway 22. The heated air stream is exhausted from the chamber 20 through an exhaust port 38 and thence through a conduit 40 to a trap 15, or drain, whereat fuel particles that may be present in the airstream are removed. In the preferred embodiment of the present invention, the air stream is heated to a temperature of 300° F. (149° C.) and controlled to provide a flow rate through the chamber 20 of 40 CFM (0.19 m$^3$/s).

In an alternate embodiment of the present invention, the heated air stream may be modified to more closely simulate various engine operating environments by introducing nitrogen ($N_2$), nitric oxide (NO), sulfur dioxide ($SO_2$), and sludge vapors into the heated air stream, preferably at a point 5 between the heat exchanger 3 and the directional valve 6. The introduction point 5 comprises a means for introducing a set of gas components including at least one of nitrogen, nitric oxide, sulfur oxide and sludge vapors into the stream of heated air and forming a mixture of heated air and at least one of nitrogen, nitric oxide, sulfur oxide and sludge vapors. The aforementioned compositions are typically present in the intake air of a combustion engine as a result of exhaust gas recirculation (EGR) and positive crankcase ventilation (PCV) systems which are often used to reduce exhaust emissions. Nitrogen, nitric oxide and sulfur dioxide can be provided directly from a bottled source. Sludge vapors can be produced by "bubbling air through a body of heated oil."

Also, in another alternative embodiment, the test piece 26 may be rotated during the test process to more closely simulate the rotatable valve arrangements frequently found in automotive engines. For this purpose, a motor 42 is mounted on a bracket 43 attached to the outer wall of the test chamber 20, and rotates the test piece 26 through a reduction gear assembly 44 and a pair of right-angle bevel gears 46, one of which is concentrically attached to the upper shaft portion of the test piece 26. If rotated during the test procedure, the test piece is preferably rotated at a rate of about 3 to 4 rpm.

The method, embodying the present invention, of determining the relative ability of a fuel, such as gasoline or diesel fuel for example, to form deposits on an engine intake valve is advantageously carried out in cooperation with the above described test apparatus. Desirably, the test parameters are optimized to encourage the deposit-forming tendencies of fuels to develop in a relatively short time, for example during a 24 hour test period. Thus, fuels can be classified relatively quickly and easily, and problem fuels identified without the need for extensive over-the-road testing in a vehicle for an extended period of time. The following test procedure is described with particular reference to such optimized test parameters.

Figure 3:
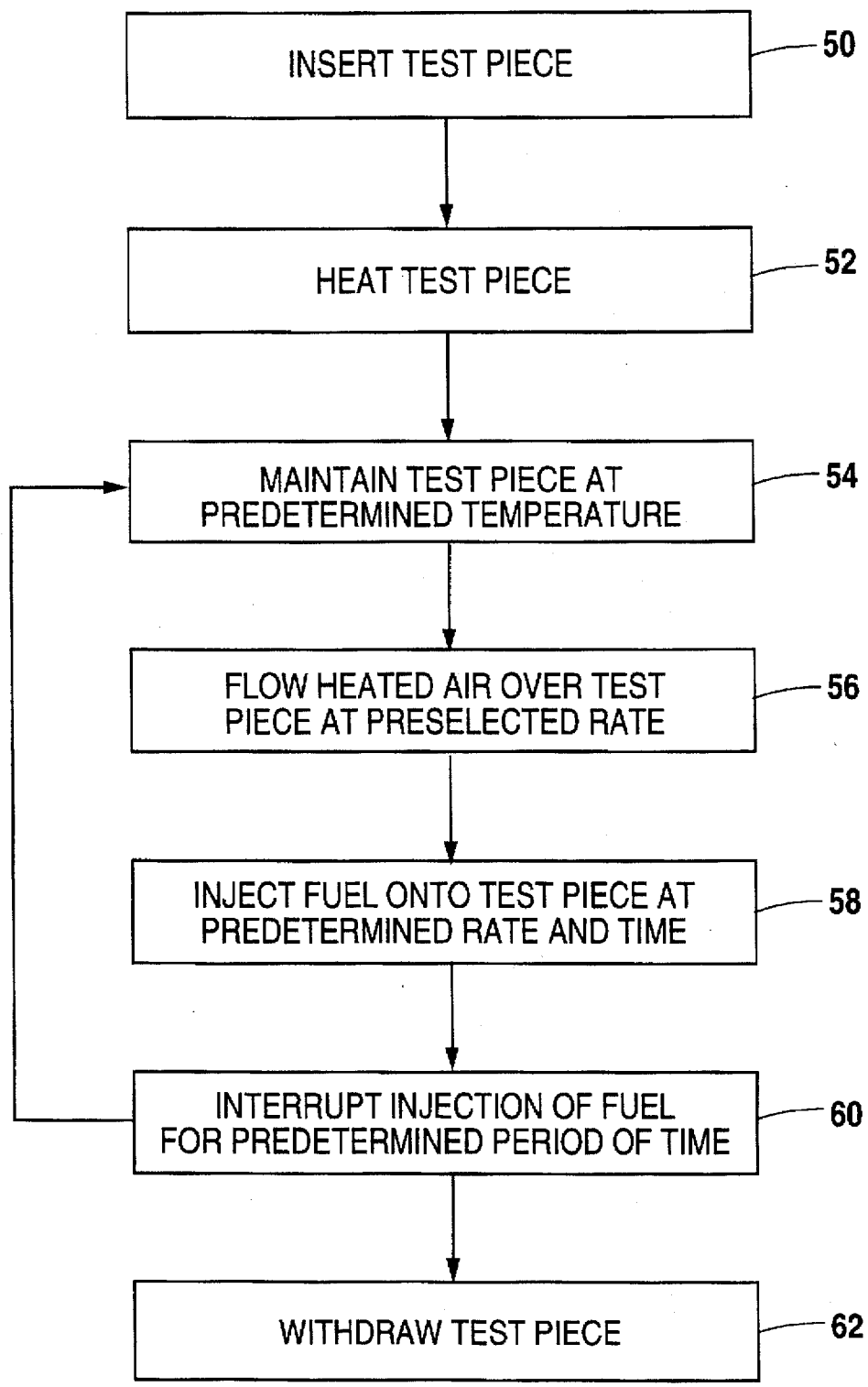
FIG. 3 is a block diagram showing the principal steps carded out in the test method embodying the present invention.

Prior to testing a preselected fuel, the test piece is carefully cleaned, dried, and weighed prior to installation in the test chamber 20. A predetermined amount of fuel, such as diesel fuel or gasoline, is pumped into the reservoir 9 and pressurized, preferably to about 38 psig, with bottled nitrogen. With reference to FIG. 3, the test procedure is initiated by inserting the test piece 26 into the chamber 20, as indicated at block 50. As represented at block 52, the test piece 26 is then heated by the internally disposed heating element 17 to a temperature, for example about 425° F. (218° C.), to provide a predetermined external temperature on the exposed test surface of, for example, about. 300° F. (149° C.)

The test piece temperature is maintained at the predetermined temperature, as shown at block 54, by assistance of the cartridge heater element 17. The internal test piece temperature is sensed by the thermocouple 28 embedded at the distal end of the heater 17, and the heater 17 controlled by the programmable controller 18 in response to the sensed temperature. Intake air is directed through the heat exchanger 3 at a preselected rate, for example about 40 CFM (0.19 m$^3$/s), heated to a temperature of about 300° F. (149° C.) and directed through the test chamber 20 whereat a flow of heated air is directed over the test piece 26, as indicated at block 56. Simultaneously, as represented by block 58, fuel is injected through the fuel injector 13 at a metered rate controlled by the programmable controller 18, which controls both the flow rate and time duration of pulsed injections. It has been found that about 1.2 ml of fuel, injected at a flow rate of 0.4 ml/s for 3 seconds followed by a one minute "soak", or drying period during which time the injection of fuel is interrupted, as indicated by block 60, advantageously optimizes the deposit-forming tendencies of many standard grades of gasoline.

The test is continuously carried out with alternating injection of fuel for three seconds followed by a one minute soak, continuous flow of heated air through the test chamber 20, and maintenance of the internal temperature of the test piece 26, for about 24 hours. If desired, the outer skin temperature of the test piece 26 can be monitored during the test by an infrared detector mounted on an inside wall of the chamber to assure that the skin temperature of the test piece 26 is maintained at a temperature of about 300° F. (149° C.).

The test piece 26 is then removed from the test chamber 20, as represented by block 62, weighed and visually examined. The increase in weight of the test piece 26 during the test is a measure of the amount of deposits formed by the test fuel during the test, and the visual inspection will indicate the type and form of the deposits.

INDUSTRIAL APPLICABILITY

The test apparatus and method embodying the present invention is particularly useful for evaluating the tendencies of automotive gasolines to form induction system deposits. With the capability of controlling all conditions in a test, this apparatus and method is also an ideal research tool.

The test chamber arrangement of the test apparatus embodying the present invention replicates a modem intake valve chamber, and the fuel reactions under different controlled test conditions can be readily evaluated. The test apparatus is fully automated and has many variable parameters including total amount of fuel used, spray volume and interval, test piece temperature, and drying time. The test method using the test apparatus provides a simple, rapid procedure for evaluation of a wide array of fuels with different deposit characteristics.

Thus, it can be seen that the test apparatus and test method embodying the present invention provide a simple, relatively quick and inexpensive means for quantitatively determining the deposit-forming characteristics of a selected fuel. Importantly, the test apparatus enables variable parameters such as temperature, air flow rate, fuel flow rate and "soak time" to be controlled in a manner such that the deposit formation rate is optimized and test results are accurately repeatable.

Although the present invention is described in terms of preferred exemplary embodiments, with specific illustrative test structure and parameters, those skilled in the art will recognize that changes in the suggested parameters and specific test apparatus may be made without departing from the spirit of the invention. For example, the method of supporting, heating, and instrumenting the work piece, and changes in the suggested temperatures and flow rates may be made to optimize the deposit-forming characteristics of a particular fuel. Such changes are intended to fall within the scope of the following claims. Other aspects, features, and advantages of the present invention may be obtained from a study of this disclosure and the drawings, along with the appended claims.

The invention:

1. A test apparatus for measuring the relative ability of a fuel to form deposits on internal parts of an engine, comprising:
   a test piece having a shape characteristic of an engine intake valve;
   a chamber having a fixture disposed therein for supporting said test piece;
   a means for heating said test piece;
   a means for sensing the temperature of said test piece and controlling the means for heating the test piece;
   a fuel injector in fluid communication with said chamber and arranged to spray fuel onto a predetermined surface area of said test piece;
   a means for heating a flowing stream of air to a selected temperature and directing said stream of heated air through said chamber; and
   a means for introducing a set of gas components including at least one of nitrogen, nitric oxide, sulfur oxide and sludge vapors into said stream of heated air and forming a mixture of said heated air and said at least one of nitrogen, nitric oxide, sulfur oxide and sludge vapors.

2. A test apparatus, as set forth in claim 1, wherein said test apparatus includes a means for rotating said test piece within said chamber.

3. A test apparatus, as set forth in claim 1, wherein said means for heating said test piece comprises an elongated electrical resistance heating element internally disposed within said test piece.

4. A test apparatus, as set forth in claim 3, wherein said means for sensing the temperature of said test piece and controlling the means for heating the test piece includes a temperature sensor disposed within said test piece and a programmable controller operatively connected to said temperature sensor and said electrical resistance heating element.

5. A test apparatus, as set forth in claim 1, wherein said apparatus includes a means for pressurizing a preselected fuel and delivering said preselected fuel to said fuel injector.

6. A test apparatus, as set forth in claim 5, wherein said means for pressurizing a preselected fuel and delivering said preselected fuel to said fuel injector includes pressurized nitrogen in fluid communication with a reservoir source of said preselected fuel.

7. A test apparatus, as set forth in claim 1, wherein said means for heating a flowing stream of air to a selected temperature and directing said stream of heated air through said chamber, includes a heat exchanger and an interconnecting conduit disposed in fluid communication with said heat exchanger and said chamber.

8. A method for measuring the relative ability of a fuel to form deposits on internal parts of an engine, comprising;
   (a) placing a test piece having the shape characteristic of an engine intake valve in a chamber;
   (b) heating said test piece;
   (c) maintaining said test piece at a predetermined temperature;
   (d) flowing a mixture of heated air and at least one of nitrogen, nitric oxide, sulfur dioxide and sludge vapors through said chamber at a preselected rate;
   (e) injecting a controlled amount of a selected fuel onto said test piece at a predetermined rate and over a first predetermined period of time;
   (f) interrupting said injecting of the selected fuel onto said test piece for drying action over a second predetermined period of time;
   (g) repeating the steps of alternately injecting and interrupting the injecting of said selected fuel while continuously maintaining said test piece at a predetermined temperature and flowing a mixture of heated air and at least one of nitrogen, nitric oxide, sulfur dioxide and sludge vapors through said chamber for a predetermined total time sufficient to establish the deposit-forming characteristic of said selected fuel.

9. A method for determining the relative ability of a fuel to form deposits on an engine intake valve, as set forth in claim 8, wherein the step of maintaining said test piece at a predetermined temperature includes maintaining the internal temperature of said test piece at a temperature of about 425° F. (218° C.).

10. A method for determining the relative ability of a fuel to form deposits on an engine intake valve, as set forth in claim 8, wherein the step of flowing a stream of heated air through said chamber at a predetermined rate includes heating said stream of air to a temperature of about 300° F. (149° C.) and flowing the stream of air heated to said temperature at a rate of about 40 CFM (0.19 m$^3$/s).

11. A method for determining the relative ability of a fuel to form deposits on an engine intake valve, as set forth in claim 8, wherein the step of injecting a controlled amount of a selected fuel onto the test piece at a controlled rate includes injecting about 1.2 ml of said selected fuel on the test piece at a rate of about 0.4 ml/s.

12. A method for determining the relative ability of a fuel to form deposits on an engine intake valve, as set forth in claim 8, wherein the step of interrupting said injecting of the selected fuel onto the test piece for a second predetermined time includes interrupting said injecting for about one minute.

13. A method for determining the relative ability of a fuel to form deposits on an engine intake valve, as set forth in claim 8, wherein the predetermined total time sufficient to establish the deposit-forming characteristic of said selected fuel is about 24 hours.

14. A method for determining the relative ability of a fuel to form deposits on an engine intake valve, as set forth in claim 8, wherein said method includes the step of rotating said test piece simultaneously with carrying out steps b through g of the method.

* * * * *